United States Patent
Gil et al.

(10) Patent No.: US 11,638,836 B2
(45) Date of Patent: *May 2, 2023

(54) STERILIZATION DEVICE UTILIZING LOW INTENSITY UV-C RADIATION AND OZONE

(71) Applicant: HEPCO HOLDINGS, LLC, Seminole, FL (US)

(72) Inventors: Patricia Carol Gil, Belleair Bluffs, FL (US); Asher Gil, Belleair Bluffs, FL (US); Daniel Gil, Madison, WI (US)

(73) Assignee: HEPCO Holdings, LLC, St. Petersburg, FL (US)

( * ) Notice: Subject to any disclaimer, the term of this patent is extended or adjusted under 35 U.S.C. 154(b) by 463 days.

This patent is subject to a terminal disclaimer.

(21) Appl. No.: 16/790,127

(22) Filed: Feb. 13, 2020

(65) Prior Publication Data

US 2020/0179718 A1 Jun. 11, 2020

Related U.S. Application Data

(63) Continuation-in-part of application No. 16/409,792, filed on May 11, 2019, now Pat. No. 10,596,282, (Continued)

(51) Int. Cl.
*A61N 5/06* (2006.01)
*A61L 2/10* (2006.01)
(Continued)

(52) U.S. Cl.
CPC .............. *A61N 5/0624* (2013.01); *A61L 2/10* (2013.01); *A61L 2/202* (2013.01); *A61L 2/24* (2013.01);
(Continued)

(58) Field of Classification Search
CPC .... A61L 2/24; A61L 2202/11; A61L 2202/14; A61L 2202/24; A61L 2202/26;
(Continued)

(56) References Cited

U.S. PATENT DOCUMENTS 2,569,079 A 10/1950 Special
5,446,289 A 8/1995 Shodeen et al.
(Continued)

FOREIGN PATENT DOCUMENTS

EP 2295112 * 3/2011
WO 2016179705 * 11/2016

OTHER PUBLICATIONS

Tianhong Dai et al., Ultraviolet C irradiation: an alternative antimicrobial approach to localized infections? 2012, Feb. 10.
(Continued)

*Primary Examiner* — Christopher A Flory
(74) *Attorney, Agent, or Firm* — Larson & Larson, P.A.; Frank Liebenow; Justin P. Miller

(57) ABSTRACT

A sterilization system uses ultraviolet radiation and ozone to eradicate deadly pathogens to sterilize a surface of an object or wound/incision site at an adjustable intensity level. The sterilization system has ultraviolet emitters that emit ultraviolet light in wavelengths that kill pathogens and in wavelengths that produce ozone at the sites, therefore killing/disabling several hard-to-kill pathogens. The sterilization system has an intensity control and proximity detectors to enable ultraviolet emission only when the system is properly located near or against the surface so as to protect from unwanted radiation from the ultraviolet light.

16 Claims, 5 Drawing Sheets

Related U.S. Application Data which is a continuation-in-part of application No. 15/683,921, filed on Aug. 23, 2017, now Pat. No. 10,335,505.

(51) Int. Cl.
*A61L 2/20* (2006.01)
*A61L 2/24* (2006.01)

(52) U.S. Cl.
CPC ........ *A61L 2202/11* (2013.01); *A61L 2202/14* (2013.01); *A61L 2202/24* (2013.01); *A61L 2202/26* (2013.01); *A61N 2005/0626* (2013.01); *A61N 2005/0642* (2013.01); *A61N 2005/0644* (2013.01); *A61N 2005/0651* (2013.01); *A61N 2005/0661* (2013.01)

(58) Field of Classification Search
CPC .... A61N 2005/0626; A61N 2005/0642; A61N 2005/0644; A61N 2005/0651; A61N 2005/0661
See application file for complete search history.

(56) References Cited

U.S. PATENT DOCUMENTS

| | | | |
|---|---|---|---|
| 6,146,588 A | 11/2000 | Deighton | |
| 7,090,649 B2 | 8/2006 | Kang | |
| 7,344,272 B2 | 3/2008 | Cooper et al. | |
| 7,875,869 B1 | 1/2011 | Shadan | |
| 7,960,706 B2 | 6/2011 | Ullman | |
| 8,241,565 B1 | 8/2012 | Abdul | |
| 8,624,202 B2 | 1/2014 | Gil et al. | |
| 8,784,731 B2 | 7/2014 | Gil et al. | |
| 2003/0088297 A1 | 5/2003 | Stoppler | |
| 2003/0153962 A1 | 8/2003 | Cumbie | |
| 2003/0163068 A1 | 8/2003 | Kang | |
| 2004/0052702 A1 | 3/2004 | Shuman | |
| 2004/0116984 A1 | 6/2004 | Spooner | |
| 2004/0262241 A1 | 12/2004 | Socha | |
| 2005/0013729 A1 | 1/2005 | Brown-Skrobot | |
| 2005/0263015 A1 | 12/2005 | Mulgrew | |
| 2006/0047329 A1 | 3/2006 | Krespi | |
| 2006/0089687 A1 | 4/2006 | Spooner | |
| 2006/0206173 A1 | 9/2006 | Gertner | |
| 2007/0075268 A1 | 4/2007 | Harris | |
| 2007/0164232 A1 | 7/2007 | Rolleri et al. | |
| 2007/0185553 A1 | 8/2007 | Kennedy | |
| 2007/0192986 A1 | 8/2007 | Garcia et al. | |
| 2007/0208395 A1 | 9/2007 | Leclerc et al. | |
| 2007/0274879 A1 | 11/2007 | Millikin | |
| 2008/0103560 A1 | 5/2008 | Powell | A61N 5/0616 607/94 |
| 2008/0172113 A1 | 7/2008 | Gourgouliatos | A61N 5/0617 607/90 |
| 2008/0208297 A1 | 8/2008 | Gertner | |
| 2008/0234786 A1 | 9/2008 | Cumbie | |
| 2008/0294227 A1 | 11/2008 | Perez | |
| 2008/0308748 A1 | 12/2008 | Burrows | |
| 2009/0065716 A1 | 3/2009 | Ullman | |
| 2009/0143842 A1 | 6/2009 | Cumbie | |
| 2009/0169426 A9 | 7/2009 | Toepfer et al. | |
| 2009/0240310 A1 | 9/2009 | Kennedy | |
| 2010/0049177 A1 | 2/2010 | Boone, III | |
| 2010/0076526 A1 | 3/2010 | Krespi | |
| 2010/0179469 A1 | 7/2010 | Hammond | |
| 2011/0037002 A1 | 2/2011 | Johnson | |
| 2011/0240883 A1 | 10/2011 | Ullman | |
| 2012/0045363 A1 | 2/2012 | Gil | |
| 2012/0310141 A1 | 12/2012 | Kornfield | |
| 2012/0328474 A1 | 12/2012 | Campagna | |
| 2013/0101461 A1 | 4/2013 | Gil et al. | |
| 2013/0336839 A1 | 12/2013 | Gil | |
| 2014/0170019 A1 | 6/2014 | Gil | |
| 2014/0222117 A1 | 8/2014 | Bourke, Jr. | |
| 2014/0264076 A1 | 9/2014 | Bettles | |
| 2014/0277299 A1 | 9/2014 | Intintoli | |
| 2015/0037201 A1 | 2/2015 | Armour | |
| 2015/0238774 A1 | 8/2015 | Anderson | |
| 2015/0359668 A1 | 12/2015 | Kornfield | |
| 2016/0101202 A1 | 4/2016 | Gil | |
| 2016/0114067 A1 | 4/2016 | Dobrinsky | A61N 5/0624 250/461.1 |
| 2016/0129279 A1 | 5/2016 | Ferolito | |
| 2016/0158575 A1 | 6/2016 | Levatter | |
| 2016/0175550 A1 | 6/2016 | Taylor | |
| 2016/0287896 A1 | 10/2016 | Anderson | A61F 13/00063 |
| 2017/0080251 A1* | 3/2017 | Yehezkel | |
| 2018/0322753 A1 | 11/2018 | Stibich | G08B 17/10 |
| 2019/0060495 A1 | 2/2019 | Gil | A61L 2/10 |
| 2019/0262487 A1 | 8/2019 | Gil | A61L 2/202 |

OTHER PUBLICATIONS

Boker, A., G. Rolz-Cruz, B. Cumbie, and A. Kimball. 2007. A single-center, prospective, open-label, pilot study of the safety, local tolerability, and efficacy of ultraviolet-C (UVC) phototherapy for the . . . Centers for Disease Control and Prevention.

Jesse Miller, Efficacy of an Ozone-Generating Whole-Shoe Disinfection Device at Three Time Points, NSF International—Applied Research Center, 789 N. Dixboro Rd. Ann Arbor, MI 48015, USA, Aug. 27, 2019.

* cited by examiner

STERILIZATION DEVICE UTILIZING LOW INTENSITY UV-C RADIATION AND OZONE

CROSS-REFERENCE TO RELATED APPLICATION

This application is a continuation-in-part of U.S. patent application Ser. No. 16/409,792 filed on May 11, 2019 issued as U.S. Pat. No. 10,596,282 on Mar. 24, 2020; which is a continuation-in-part of U.S. patent application Ser. No. 15/683,921 issued as U.S. Pat. No. 10,335,505 on Jul. 2, 2019, the disclosures of both are incorporated by reference.

FIELD

This invention relates to the field of medicine and more particularly to a system for sterilizing objects such as the skin of a human or medical devices.

BACKGROUND

The rising problem of antibiotic resistance has led to fears that medicine will return to the situation of a century ago when extensive wounds and surgery often led to death due to uncontrollable infection. These fears have in turn spurred a major research effort to find alternative antimicrobial approaches which, it is hypothesized, will kill resistant micro-organisms while being unlikely to cause resistance to develop to themselves. At the present time many international research efforts to discovery new antimicrobials are underway. Recently, the emphasis is on how to take precautions against creating, and if possible eliminate multidrug resistance in concert with exploring new methods to kill pathogenic microorganisms. Karen et al. in "Tackling antibiotic resistance," Bush K, *Nat Rev Microbiol.* 2011 Nov. 2; 9(12):894-6, recently pointed out that the investigation of novel non-antibiotic approaches, which can prevent and protect against infectious diseases should be encouraged, and should be looked upon as a high-priority for research and development projects.

The best known source of sterilization is UV-C radiation (wavelength: 200-280 nm). Among this wavelength range, the optimum range of 250-270 nm has the optimum potential ability to inactive microorganisms because it is strongly and mainly absorbed by nucleic acids of microbial cells and, therefore is the most lethal range of wavelengths.

The bactericidal mechanism of UV-C is to cause damage to their RNA and DNA, which often leads to the formation of dimers between pyrimidine residues in the nucleic acid strands. The consequence of this modification is that the production of cyclobutane pyrimidine dimers (CPDs) causes deformation of the DNA molecule, which might cause defects in cell replication and lead to cell death afterwards.

It is well known that prolonged and repeated exposure to UV irradiation can damage host cells and be particularly hazardous to human skin. As to long-term UVC irradiation of human skin, it is also known to have potential carcinogenicity. When UVC irradiation is applied to treat localized infections, one must consider the possible side-effects of UVC delivered at effective antimicrobial fluences on normal mammalian cells and tissue. The safety issue of UVC germicidal treatment requires that the pathogenic microbe is selectively eradicated while the normal tissue cells are spared.

It has been found that no significant adverse effects were induced in human primary corneal epithelial cells when the cells were exposed to 1.93 mJ/cm2 UVC (265 nm), which induced 100% inhibition of growth of all the bacterial species cultured on agar plates. UVC has been used to reduce pathogen contamination of platelet concentrates. The results showed UVC inactivated more than 4 log 10 Gram-positive *S. aureus, Bacillus cereus* and *S. epidermidis*, and Gram-negative *E. coli, P. aeruginosa* and *Klebsiella pneumoniae*.

Most of the experimental results mentioned above suggest that UVC at appropriate fluences does not cause significant damages to host cells and tissues. However, UVC irradiation still has potential to induce nonspecific damage. Studies demonstrated that the DNA of mammalian cells could indeed be damaged by UVC at its effective antimicrobial fluences. Fortunately however, at the same time, the DNA repairing enzymes of the host cells could rapidly repair the damaged DNA. In addition, to minimize the UVC-induced non-specific damage, the intact skin around the area to be treated could be shielded from UVC illumination. On the other hand, application of UVC is limited in some special locations due to its detrimental effects such as infections of the eyes.

A study presented by Taylor et al., reported that the mean bacterial CFU in joint arthroplasty surgical wounds was reduced by 87% with 0.1 mW/cm2 (P<0.001) and 92% with 0.3 mW/cm2 (P<0.001) of UVC. Thai et al. used UVC irradiation to treat cutaneous ulcers infected with MRSA. In all three patients, UVC treatment reduced the bacterial burden in wounds and promoted wound healing. Two patients had complete wound closure following 1 week of UVC treatment. Another trial was carried out by the same investigators in 22 patients with chronic ulcers manifesting at least two signs of infection and critically colonized with bacteria. The patients received a single UVC treatment and demonstrated significantly reductions of the bacterial burden. In a study, thirty patients with mild-to-moderate toenail onychomycosis were used to treat with UVC. Improvement by at least 1 measurement point was achieved in 60% of patient at 16-week follow-up compared with baseline. There were some unusual and slight side effects such as temporary mild eythema of the treated toe. In addition to the inactivation of microbial cells in the cutaneous wound, UVC exposure is beneficial for wound healing by promoting the expression of basic fibroblast growth factor (bFGF) and transforming growth factor, although the exact mechanisms of UVC for wound healing is still unclear. Others have investigated the prophylactic efficacies of UVC irradiation in 18 cases of catheter exit-site infections. Although five cases remained unchanged, ten cases (55%) became culture negative and a further three cases showed a microbial decrease.

In summary, it has been known during the past one-hundred years that UVC irradiation is highly bactericidal; however, using UVC illumination for the prophylaxis and treatment of localized infections is still at very early stages of development. Most of the studies are limited to in vitro and ex vivo levels, while in vivo animal studies and clinical studies are much rarer. A major advantage of using UVC over antibiotics is that UVC can eradicate resistant and pathogenic microorganisms much more rapidly without any systemic side-effects. UVC may also be much more cost effective than the commonly used antibiotics.

As can be seen, there is a delicate balance between killing pathogens on a surface (e.g., skin, instruments) and emitting too much UVC so as to damage the skin or affect one's eyesight. In the past, others have disclosed devices that are intended to kill pathogens through UV emission, for example, US Pat. Pub. 20110037002 to Johnson, but these devices rely heavily on human operation, including triggers that require a human to judge when sufficient radiation is emitted to kill the anticipated pathogens while limiting the amount of radiation to safe levels for human coexistence. Having a trigger creates a reliance upon the user to hold the trigger for an appropriate amount of time, enough time to kill the pathogens and not too much time as to damage the target material or tissue.

What is needed is a system/device that will expose an object (e.g., instrument) or a locale of a human (or animal) to UVC and ozone to reduce or eliminate pathogens.

SUMMARY

The disclosed system for directly radiating an object or skin generally relates to using UV-C radiation in combination with ozone to eradicate deadly pathogens (germs and viruses, spores and fungus) for sterilization. In some embodiments, t disclosed system relates to a device that will be used both prior to surgery and/or prior to closing an incision following surgery. In some embodiments, the disclosed system is activated by a person placing the head of the device above the wound/incision site and activating the sterilization process by, for example, stepping on a foot control device. Once activated, the device will activate UV-C bulbs that emit UV-C radiation and ozone to sterilize objects or the wound/incision site. Both UV-C radiation and ozone are provided to kill/neutralize certain pathogens that are not killed/neutralized by ultraviolet light alone. The devices, wound, incision site, or pre-incision site will be exposed for a time specified by and controlled by, for example, an electronic timer or programmatic delay.

In one embodiment, a system for directly radiating skin is disclosed including an enclosure having one or more ultraviolet emitters housed therein and configured to selectively emit ultraviolet light from the housing onto a surface where the ultraviolet light produces ozone at the surface. There is a mechanism for detecting contact with the surface and a mechanism for connecting a source of power to the one or more ultraviolet emitters for a period of time responsive to detecting that the enclosure is positioned against the surface.

In another embodiment, a method of radiating skin is disclosed including providing a system that selectively emits ultraviolet light. The system has one or more skin contact detectors. The system that selectively emits ultraviolet light is placed against skin, thereby the one or more skin contact detectors detecting contact with the skin. Responsive to detecting the system being placed against the skin, the system that selectively emits ultraviolet light emits the ultraviolet light and the ultraviolet light and produces ozone at the skin. After delaying for a period of time, the system that selectively emits ultraviolet light is disabled, thereby stopping emission of the ultraviolet light and stopping production of the ozone.

In another embodiment, a system for radiating skin is disclosed including an enclosure having therein one or more ultraviolet emitters that are covered by a filter. The filter passes ultraviolet light from the one or more ultraviolet emitters. The one or more ultraviolet emitters are configured to emit ultraviolet light from the housing, through the filters, and onto a surface of the skin where ozone is produced by the ultra-violet light. There is a mechanism for detecting contact with the surface of the skin that is configured to prevent the one or more ultraviolet emitters from emitting the ultraviolet light until contact is made with the surface of the skin and there is a timer that is configured to connect a source of power to the one or more ultraviolet emitters for a period of time responsive to the contact being made with the surface of the skin.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
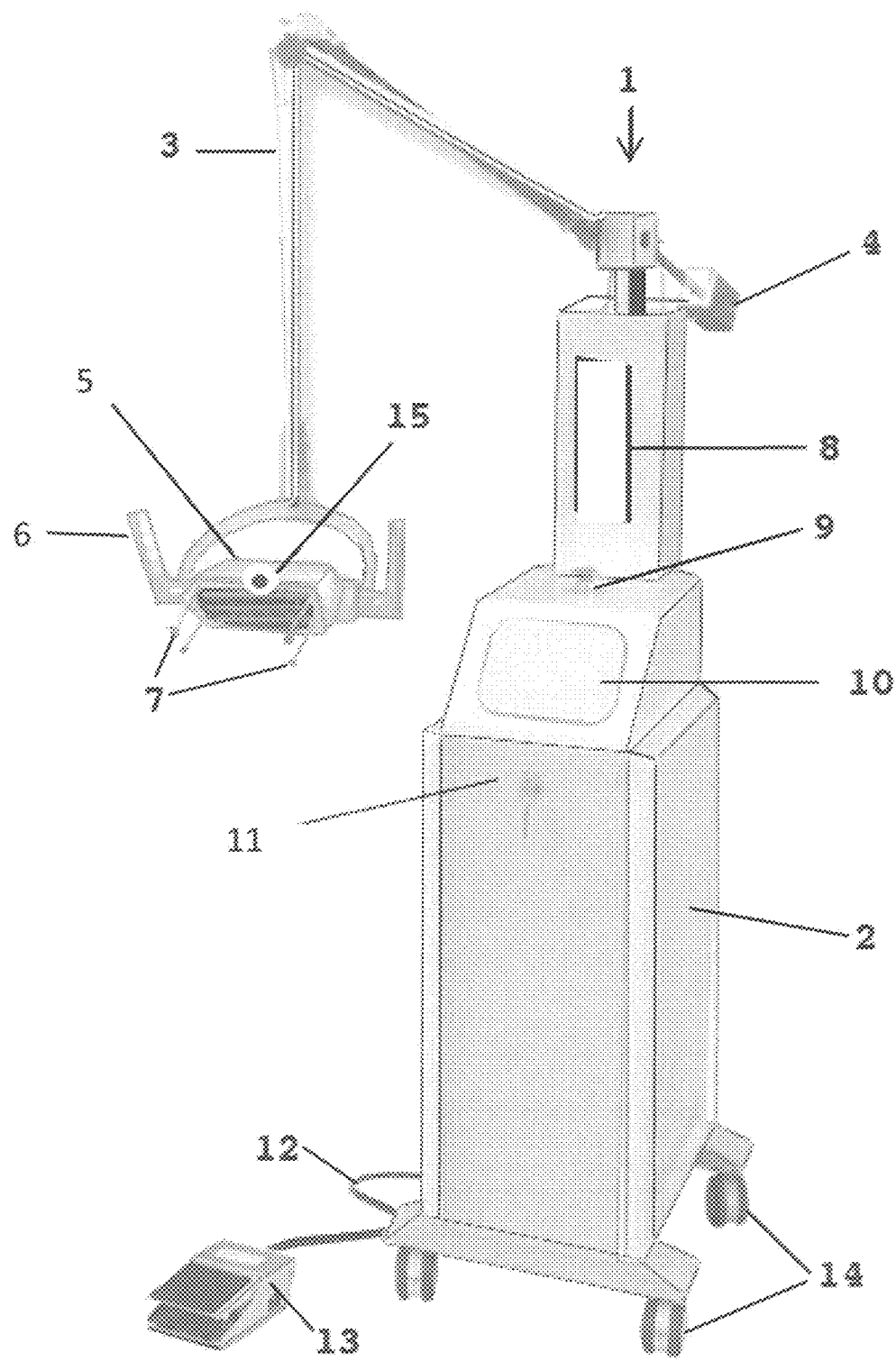
FIG. 1 is a perspective view of a system for directly radiating skin.

Reference will now be made in detail to the presently preferred embodiments of the invention, examples of which are illustrated in the accompanying drawings. Throughout the following detailed description, the same reference numerals refer to the same elements in all figures.

Throughout this description, the term "sterilize" is used to describe the act of killing pathogens. Although "sterile" often refers to something being void of pathogens, the term "sterilize" is the process of destroying (killing or disabling) microorganisms, as it is anticipated that most or all pathogens will be destroyed, though depending on UVC dosage and ozone exposure, it is anticipated that not all pathogens will be destroyed with each use of the described apparatus.

Throughout this description, the system is described as a system to directly radiate a surface (e.g., a wound), for example, an area in which an incision will be made, an incision that was made during an operation, either an open incision or a closed incision—closed by, for example, stitches, medical instruments, etc. The wound is also anticipated to be a wound that has occurred by accident (e.g., an abrasion or dog bite) or due to an ailment such as a bed sore, etc. There is no limitation on how the described system is used. For example, it is fully anticipated that the described system be used to radiate an area of skin where there is no wound, for example, before an incision is made, etc.

Ultraviolet radiation is well known for its ability to eradicate deadly pathogens. However, the time required to do so is a serious consideration as extended exposure to UV-C has the potential of being harmful to tissue/skin around wound/incision sites. The system for directly radiating a wound herein described circumvents the potential dangers of exposure by reducing the time necessary for eradication of deadly pathogens by incorporating a short burst of ozone. The ozone acts as a catalyst to destroy the protective membrane (shell) that surrounds certain pathogens that are capable of causing an infection that is capable of leading to death. By reducing the time needed to expose the surrounding skin the system for directly radiating a wound reduces potential dangers of exposure to UV-C and at the same time reduces the time necessary for the sterilization process.

The invention generally relates to using ultraviolet radiation in combination with ozone to eradicate deadly pathogens (germs and viruses, spores and fungus) to sterilize, for example, an object or a wound/incision site. The invention relates to a system for directly radiating a surface of an object or a wound either prior to surgery, prior to closing an incision following surgery, or at any time. This system for directly radiating a surface is activated, for example, by a person placing the head of the device above the surface, wound/incision and initiating UV-C bulbs to therefore emit ozone which will sterilize (kills a number of pathogens) at the wound/incision site using UV-C radiation and ozone. The surface or wound/incision site will be exposed for a time specified by and controlled by an electronic timer that begins by, for example, when the device is at an appropriate proximity to the target wound/incision site. Once activated, the system for directly radiating a surface produces both UV-C and ozone on the surface/wound/incision area. For example, the period of time is from 5 to 100 seconds, which is sufficient to kill/disable pathogens but short enough to prevent damage to the skin.

Figure 2:
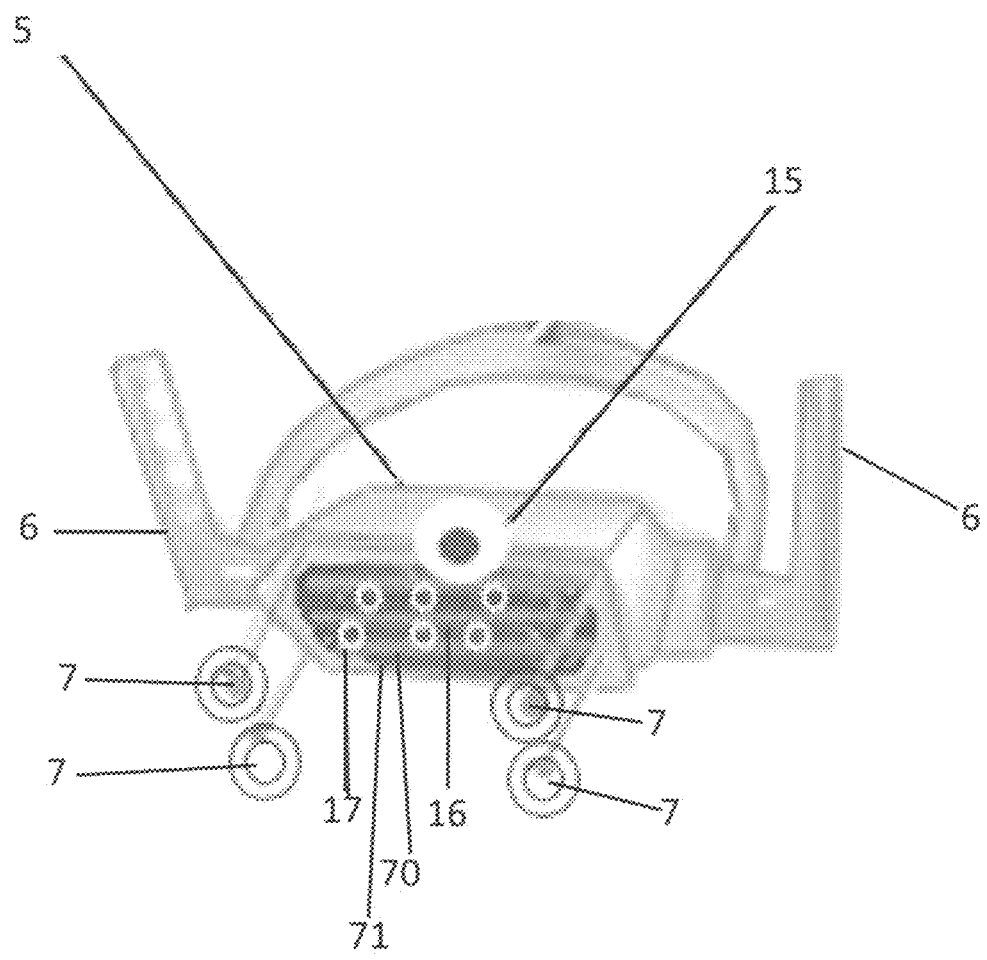
FIG. 2 is a perspective view of a device head showing some of the components incorporated in the head of the system for directly radiating skin.
Figure 3:
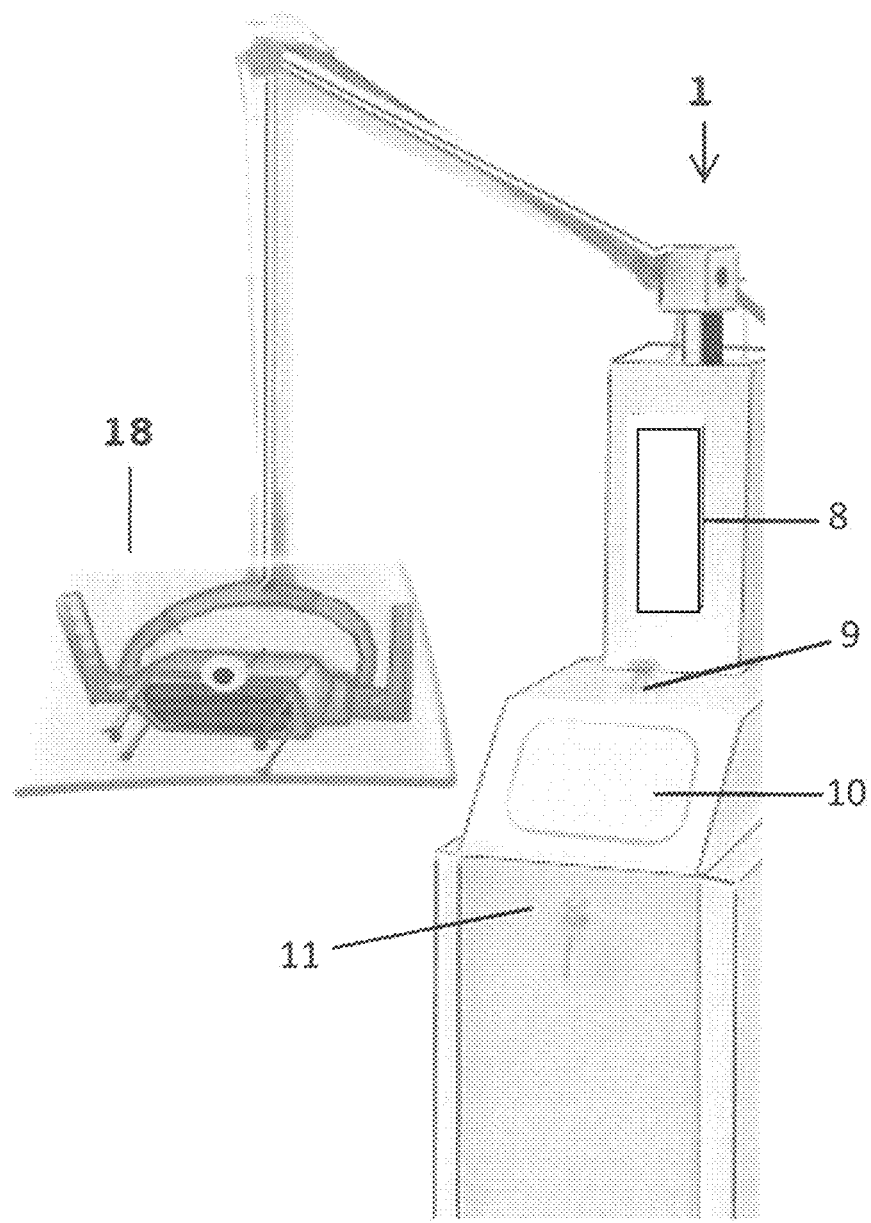
FIG. 3 is a perspective view of the device head showing a protective shield.
Figure 5:
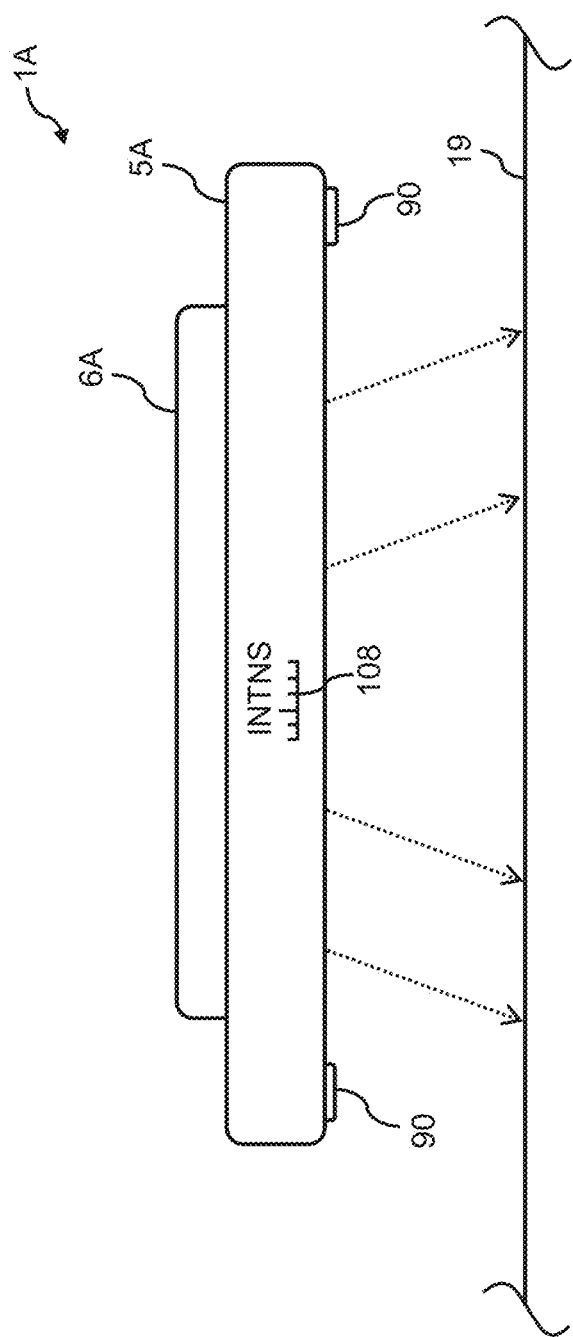
FIG. 5 illustrates a hand-held version of the system for directly radiating objects.

Although shown attached to an articulating arm 3 in FIGS. 1-3, it is equally anticipated that the system for directly radiating objects 1 is hand-held as shown in FIG. 5, for example, held by a person over a target surface 15 such as a wound, a scalpel, bedsheets, etc.

In some embodiments, the system for directly radiating a surface described herein incorporates a protective shield that is designed to direct the UV-C plus ozone light to the wound/incision site and at the same time protecting the user from unnecessary exposure the both UV-C and ozone.

In some embodiments, the system for directly radiating a surface or wound incorporates safety sensors to ensure that the device is activated only when it is in optimal position. This prevents the system for directly radiating a surface from emitting UV-C until it is in position (e.g., against the patient's skin).

In a report titled, "Ultraviolet C irradiation: an alternative antimicrobial approach to localized infections?", by Dai Tianhong et al., it is reported that the mean bacterial CFU in joint arthroplasty surgical wounds was reduced by 87% with 0.1 mW/cm$^2$ (P<0.001) and 92% with 0.3 mW/cm$^2$ (P<0.001) of UVC. Thaihong et al. used UVC irradiation to treat cutaneous ulcers infected with MRSA. In all three patients, UVC treatment reduced the bacterial burden in wounds and promoted wound healing. Two patients had complete wound closure following 1 week of UVC treatment. Another trial was carried out by the same investigators in 22 patients with chronic ulcers manifesting at least two signs of infection and critically colonized with bacteria. The patients received a single UVC treatment and demonstrated significantly reductions of the bacterial burden.

Boker et al., "A single-center, prospective, open-label, pilot study of the safety, local tolerability, and efficacy of ultraviolet-C (UVC) phototherapy" describes a study that enrolled thirty patients with mild-to-moderate toenail onychomycosis to treat with UVC. Improvement by at least 1 measurement point was achieved in 60% of patient at 16-week follow-up compared with baseline. There were some unusual and slight side effects such as temporary mild eythema of the treated toe. In addition to the inactivation of microbial cells in the cutaneous wound, UVC exposure is beneficial for wound healing by promoting the expression of basic fibroblast growth factor (bFGF) and transforming growth factor, although the exact mechanisms of UVC for wound healing is still unclear.

The Dai Tianhong report cites Shimomura et al. as having investigated the prophylactic efficacies of UVC irradiation in 68 cases of catheter exit-site infections. Although five cases remained unchanged, ten cases (55%) became culture negative and a further three cases showed a microbial decrease.

In "Efficacy of an Ozone-Generating Whole-Shoe Disinfection Device at Three Time Points," 27 Aug. 2019, by NSF International Laboratories, efficacy of a device that emits UVC as well as ozone aimed at the sole of a shoe is analyzed. The tests were performed by exposing cultures of various pathogens to UVC and ozone for various amounts of time (6, 8, and 10 seconds), for example, showing 99.8% to 99.9% reduction in MRSA. The device tested emits a fixed amount of UVC (and hence ozone) for a fixed amount of time, but does not have the ability to adjust the time and/or intensity of the UVC, and hence, ozone generation.

Referring to FIG. 1, a perspective view of an embodiment of the system for directly radiating objects 1 is shown in an exemplary physical embodiment. This embodiment of the system for directly radiating objects 1 includes a base 2 for housing electrical components (see FIG. 4), an articulating arm 3 hingedly connected to the base, an optional counterweight 4, a head 5 having there within the ultraviolet emitters 70 (see FIG. 4) that also emit ozone, optional handles 6, position sensors 7, a computer display 8, indicator light 9 (e.g., LEDs), a control panel 10, an optional lock 11, electrical cord 12, an optional foot control 13, wheels 14 and a camera 15. Although shown as a floor-based system, it is fully anticipated that system for directly radiating objects 1 be embodied in a hand-held device 1A including the head 5 with all controls, ultraviolet emitters 70, etc., contained there within the head 5 (see FIG. 5).

Note that in the embodiment of FIGS. 1-3, the position sensors 7 are located around a periphery of the head 5 such that, when the head 5 is positioned over a zone of a surface to be radiated with the ultraviolet light, the position sensors 7 contact only peripheral areas of the zone of the surface so as to not apply pressure to, for example, a wound or incision.

The ultraviolet emitters 70 preferably emit ultraviolet radiation at wavelengths that kill/disable pathogens and also generate ozone, as ozone is a gas that is known to aid in the destruction/disablement of certain pathogens that may not be killed solely by ultraviolet light. For example, the ultraviolet emitters 70 emit at a wavelength of around 254 nm to kill/disable many pathogens and emit at a wavelength of 185 nm to generate ozone to kill/disable some hard to kill pathogens such as MRSA, etc. In such, it is fully anticipated that a single ultraviolet emitter 70 emit both wavelengths of radiation or some of the ultraviolet emitters 70 emit at one wavelength of radiation and other of the ultraviolet emitters 70 emit at another wavelength of radiation. There is no limitation on the types and configuration of ultraviolet emitters 70 as long as the requisite wavelengths of radiation are emitted and directed towards the wound to kill/disable pathogens in the area of the wound.

Referring to FIG. 2 is a perspective view of the above described embodiment of the system for directly radiating objects 1 showing details of the head 5, position sensors 7, handles 6, and one or more ultraviolet emitting bulbs 70. In some embodiments, there are additional LEDs 17 to shed visible light on the patient while positioning the head 5. This emission of visible light aids in locating of the head as well as providing feedback to the technician as to where the ultraviolet light is or will be irradiating, as ultraviolet light is not visible to humans.

The head 5 includes one or more ultraviolet emitters 70 (e.g., ultraviolet emitting tubes, ultraviolet emitting light emitting diodes or LEDs, etc.) and, for protection from electrical shock, it is preferred that the one or more ultraviolet emitting bulbs 70 be protected by a cover 71 that is made of a sturdy material that efficiently passes ultraviolet light in both the wavelengths that are known to kill/neutralize pathogens (e.g., 254 nm) and wavelengths that are known to create the requisite ozone ($O_3$) (e.g., 185 nm). In some embodiments, the cover 71 comprises fused silica. In a less preferred embodiment, the cover comprises fused quartz.

Referring to FIG. 3 is a perspective view of the above described embodiment of the system for directly radiating objects 1 showing a protective shield 18. The protective shield 18 is made of a pliable material such as rubber or soft plastic that, when pressed against, for example, a patient's skin, conforms to contours of the patient's skin, thereby sealing against the patient's skin and reducing emissions of ultraviolet light from the one or more ultraviolet emitting bulbs 70, as such emissions have the potential to affect the technician's and doctor's eyesight. As it is difficult to see ultraviolet light (human eyes typically do not visualize ultraviolet light), the optional LEDs 17 provide visible light emanating from the head 5, beneath the protective shield 18. Therefore, should the protective shield 18 not seal properly against the surface or patient's skin, the technician/doctor is able to see the visible light and can adjust the head 5 or stop operation of the one or more ultraviolet emitting bulbs 70.

Figure 4:
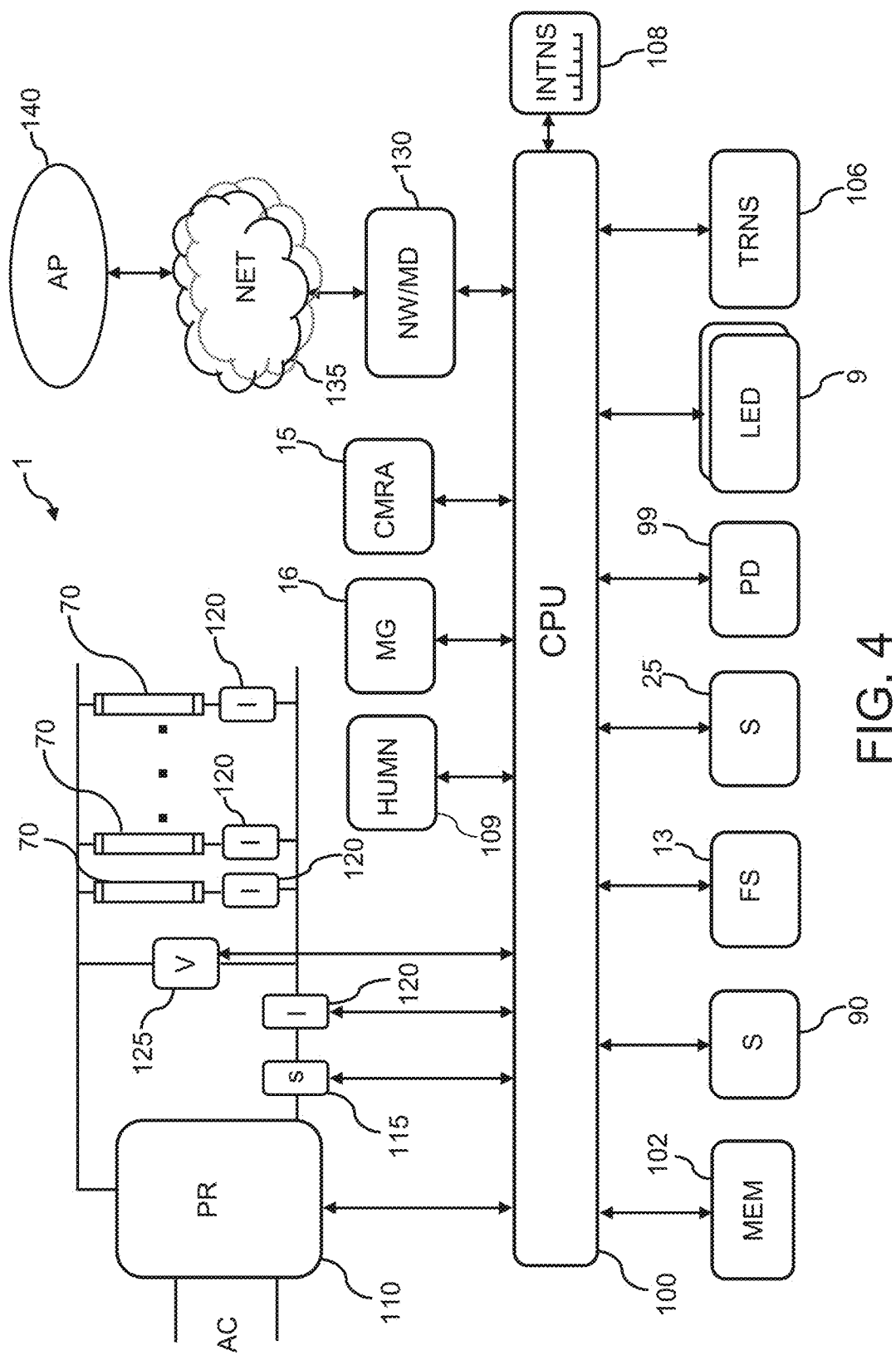
FIG. 4 is a schematic diagram of the system for directly radiating skin.

Referring to FIG. 4, block diagram showing an exemplary electrical sub-system 96 of the system for directly radiating objects 1 is shown. This is an example of one implementation, utilizing a processor 100 to control operation of the system for directly radiating objects 1. There are many other implementations anticipated, with or without the use of a processor 100 or processing element 100.

The exemplary processor-based sub-system 96 is shown having a single processor 100, though any number of processors 100 is anticipated. Many different computer architectures are known that accomplish similar results in a similar fashion and, again, the present invention is not limited in any way to any particular processor 100 or computer system. In this exemplary processor-based sub-system 96, the processor 100 executes or runs stored programs that are generally stored for execution within a memory 102. The processor 100 is any processor or a group of processors, for example an Intel 80051 or processors that are known as Programmable Logic Controllers (PLCs).

The memory 102 is connected to the processor as known in the industry and the memory 102 is any memory or combination of memory types suitable for operation with the processor 100, such as SRAM, DRAM, SDRAM, RDRAM, DDR, DDR-2, flash, EPROM, EEPROM, etc. The processor 100 is connected to various devices (e.g., sensors, relays, lights, etc.) by any known direct or bus connection.

For AC powered operation, AC power is conditioned and regulated by a power regulator 110, as known in the industry. The power regulator 110 provides power for operation of the one or more devices that emit ultraviolet radiation 70, for the processor 100, and for any other component of the processor-based sub-system 96. In this example, one or more devices that emit ultraviolet radiation 70 are ultraviolet emitting bulbs 70, similar in operation to small florescent bulbs, though the present invention is not limited to any particular devices that emit ultraviolet radiation 70; as ultraviolet emitting LEDs or any ultraviolet emitter is anticipated. In general, such devices that emit ultraviolet radiation 70 operate at a specific voltage and draw a typical amount of current per specifications from suppliers of such devices that emit ultraviolet radiation 70. As the devices that emit ultraviolet radiation 70 age or fail, in some embodiments, such aging or failure is detected by monitoring of the current and/or voltage provided to the devices that emit ultraviolet radiation 70 by one or more sensors 120/125. For example, one sensor 125 monitors voltage over the devices that emit ultraviolet radiation 70 and another sensor 120 monitors current to/from the devices that emit ultraviolet radiation 70. Outputs of the sensors 120/125 are connected to the processor 100. Upon detection of a failed or aging devices that emit ultraviolet radiation 70, the processor 100 signals such aging or failure by eliminating one or more lamps or LEDs 9, changing the color of one or more lamps or LEDs 9, emitting a sound through a transducer 106, and/or sending a message through the network 135 to, for example, an operations system (computer) 140 that is connected to the network 135. In such, the system for directly radiating objects 1 includes a network adapter or modem 130 to enable communication through the network 135, for example, an operations processor 140.

It is important that a certain number of devices that emit ultraviolet radiation 70 are functioning in order to properly radiate the target surface and kill sufficient pathogens. Being that it is difficult to discern if any of the devices that emit ultraviolet radiation 70 have failed because the devices that emit ultraviolet radiation 70 typically do not emit visible light and/or because it is harmful to expose one's eye to the light emitted by the devices that emit ultraviolet radiation 70, in some embodiments, separate current sensors 120 are configured in series with each of the devices that emit ultraviolet radiation 70. In such, the processor 100 reads the current going to/from each of the devices that emit ultraviolet radiation 70 and the processor 100 indicates which device(s) that emit ultraviolet radiation 70 has aged or failed by illuminating the lamps/LEDs 9 in a certain pattern, colors, or sequence (e.g., blinking 3 times if the third device that emits ultraviolet 70 has failed) and/or encoding an indication of the failed devices that emit ultraviolet radiation 70 in a message that is sent through the network 135 to an operations system 140.

Also in this example, one or more sensors 90, magnetic sensors 16, and/or pressure sensors 25 are interfaced to the processor 100. Any known and/or future sensor 90/25 that detects proper placement is anticipated and is connected to the processor 100. In the examples shown in FIGS. 1-3, position sensors 7 are activated as the head 5 of the exemplary system for directly radiating objects 1 is pushed against the patient's body or a surface 15 (see FIG. 5), for example using sensors 25 that are micro switches. There are many known proximity detectors, including pressure sensors 25 to detect pressure of the head 5 against the surface to be sterilized, ultrasonic distance sensor (sonar), skin continuity sensors, mechanical switches (e.g., coupled to the position sensors), ambient light detectors, cameras 15, magnetic sensors 16, etc. Magnetic sensors 16 are anticipated for use in sterilizing metallic medical objects such as surgical devices, etc. In this, as the head 5 the exemplary system for directly radiating objects 1 nears the medical object; the magnetic sensor detects the medical object and initiates operation of the ultraviolet light and ozone. After sufficient exposure, the medical object is turned over and as the head 5 the exemplary system for directly radiating objects 1 nears the second side of the medical object; the magnetic sensor detects the medical object and initiates operation of the ultraviolet light and ozone. This kills pathogens on both sides of the medical object.

The processor monitors the status of the sensor(s) 90/25 and enables or disables operation of the devices that emit ultraviolet radiation 70 through operation of a power switching device 115 (e.g., solid-state switch or relay). In such, it is also anticipated that the processor 100 illuminate one or more indicators 9 or LEDs to signal that the devices that emit ultraviolet radiation 70 are operating after detection of proper placement of the head 5 against the patient and after supplying power to the devices that emit ultraviolet radiation 70 through operation of the power switching device 115.

In some embodiments, after the processor 100 detects the proper placement of the head 5 against the patient by way of, for example sensor(s) 90/25), the processor 100 closes the power switching device 115, thereby illuminating the device(s) that emit ultraviolet radiation 70 for emission of the ultraviolet light onto the patient (e.g., at a location prior to or after an incision is made).

In some embodiments, after the processor 100 detects the proper placement of the head 5 against the patient or surface, the processor 100 controls the power switching device 115 to provide an adjustable/settable flow of current to the device(s) that emit ultraviolet radiation 70. In this, the processor monitors either or both of an intensity setting 108 and/or a human operation setting 109. Based upon the settings of either or both of an intensity setting 108 and/or a human operation setting 9, the processor controls the current flow to the illuminating the device(s) that emit ultraviolet radiation 70, thereby providing a settable range of emission of the ultraviolet light onto the patient (e.g., at a location prior to or after an incision is made) or object. For example, if used on human skin, the human operation setting 109 is set to on, thereby limiting the ultraviolet emission intensity to what is recommended for human skin and, in some embodiments, further controlled by the intensity setting 108 (e.g., an up/down control, slide control, rotating control) to set an intensity level depending upon the anticipated microorganisms so that the human skin is not burned. If used on an instrument, then the human operation setting 109 is set to off and the intensity is controlled by the intensity setting 108 (e.g., an up/down control, slide control, rotating control) to a level depending upon the anticipated microorganisms.

As some device(s) that emit ultraviolet radiation 70 do not have a range of emission capabilities, in some embodiments, the processor 100 modulates the current provided to the device(s) that emit ultraviolet radiation 70 by switching on/off the power switching device 115. In some embodiments, individual device(s) that emit ultraviolet radiation 70 are controlled by, for example, multiple power switching devices 115, in series with each of the sensors 120. In this way, when multiple device(s) that emit ultraviolet radiation 70 are present, for lower emissions, less device(s) that emit ultraviolet radiation 70 are illuminated.

In some embodiments, the processor 100 also illuminates one or more lamps/LEDs 9 when the device(s) that emit ultraviolet radiation 70 are operational to provide feedback to the technician that the sterilization process is in operation. In some embodiments, the processor 100 retains power to the devices that emit ultraviolet radiation 70 until it is detected that the technician has moved the head 5 away from the patient's body. In other embodiments, the processor 100 retains power to devices that emit ultraviolet radiation 70 for a fixed or settable length of time. In either embodiment, once the devices that emit ultraviolet radiation 70 are shut off, any lamps/LEDs 9 that were illuminated are extinguished to indicate to the user that the sterilization has stopped and it is safe to move the head 5. It is anticipated that, in some embodiments, a display 8 provides instructions and the technician operates the system for directly radiating objects 1 through a control panel 10, for example, a touch screen control panel or a keyboard, or any other known input device.

In some embodiments, operation of the system for directly radiating objects 1 is controlled by a foot control 13, for example, pressing the foot control 13 turns on the devices that emit ultraviolet radiation 70 and/or initiates a timer that turns on the devices that emit ultraviolet radiation 70 for a period of time.

In some embodiments, the system for directly radiating objects 1 includes one or more proximity detectors 99 that are interfaced to the processor as known in the industry, for example through a Universal Serial Bus interface (USB), a serial interface such as RS-232 or RS-422, RS-485, wireless connection, etc. In such, the proximity detectors 99 are, for example, bar code readers (e.g., QR code or any type of bar code), Radio Frequency Identification Device (RFID) readers, facial recognition devices, retinal scanning devices, fingerprint scanners, etc. In such, the system for directly radiating objects 1 communicates with the remote operations system to retrieve patient records related to the patient being treated and, in some embodiments, the patient records are used to make system settings controlling the operation of the system for directly radiating objects 1, for example, the emission power and/or the duration of emission.

The processor 100 initiates operation of the devices that emit ultraviolet radiation 70 through, for example, the power switching device 115 to start the reduction of pathogens in the exposed area of the patient's body. The processor indicates operation by, for example, illuminating one or more of the indicators 9 (e.g., LEDs), in some embodiments with a specific color, sequence, pattern, etc. In some embodiments, the processor terminates the ultraviolet emission through, for example, the power switching device 115 after a period of time, which is either predetermined globally, predetermined based upon the identification of the user as determined by the one or more proximity detectors 99. It is anticipated that the processor 100 query the remote operations system 140 to obtain information regarding the amount of exposure time, user identities, passwords/pins, current environmental conditions, pathogen alerts, etc. it is also anticipated that the system for directly radiating objects 1 include one or more environmental sensors (not shown), coupled to the processor 100 such as temperature sensors and humidity sensors, etc.

In some embodiments, once the processor 100 terminates the ultraviolet emission, the processor notifies the user that the user of completion by, for example, illuminating or blanking one or more of the indicators 9 (e.g., LEDs), in some embodiments with a specific color, sequence, pattern, etc. Also, in some embodiments, a completion record is created for the user. The completion record is transmitted to the operations processor 140 through the network 135, stored in the memory 102 for later retrieval, etc.

Referring to FIG. 5, a hand-held version of the system for directly radiating objects 1A is shown. In this, an optional handle 6A is provided. The sensors 90 (e.g., proximity sensors, ultrasonic distance sensors, etc.) detect proximity to a target surface 19 of the object/skin that is to be radiated with ultraviolet light (UVC) and, hence doused with ozone, Upon detecting proximity to the target surface by the sensors 90, the the devices that emit ultraviolet radiation 70 (not shown in FIG. 5) are activated for a preset period of time and, in some embodiments, at a settable intensity as per an intensity setting device 108.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A system for killing pathogens present on a surface, the system comprising:
    an enclosure;
    an intensity control for setting an ultraviolet intensity, the intensity control mechanically interfaced to the enclosure;
    one or more ultraviolet emitters housed within the enclosure and configured to selectively emit ultraviolet light from the enclosure onto the surface, the ultraviolet light configured to produce ozone at the surface, an intensity of the ultraviolet light proportional to a setting of the intensity control; one or more sensors for detecting the proximity to the surface comprising an ultrasonic distance measuring system; and
    a timer, the timer connecting a source of power to the one or more ultraviolet emitters, and responsive to the timer, the ultraviolet emitters emit the ultraviolet light at the intensity for a period of time responsive to the one or more sensors detecting proximity to the surface.

2. The system of claim 1, further comprising a switch for indicating that the ultraviolet light is to be directed at a living being and, responsive to activating the switch, the intensity is limited to an acceptable intensity for the living being.

3. The system of claim 1, wherein the ultraviolet emitters are controlled by varying an electrical current presented to the ultraviolet emitters to emit the ultraviolet light at the intensity.

4. The system of claim 1, wherein the ultraviolet emitters are controlled by modulating an electrical current presented to the ultraviolet emitters to emit the ultraviolet light at the intensity.

5. The system of claim 1, wherein the one or more ultraviolet emitters comprise one or more ultraviolet emitting tubes.

6. The system of claim 1, wherein the one or more ultraviolet emitters comprise one or more ultraviolet light emitting diodes.

7. The system of claim 1, wherein the one or more sensors for detecting the proximity to the surface comprises a magnetic sensor.

8. The system of claim 1, further comprising an electric current sensor interfaced in series with each of the one or more ultraviolet emitters and if during when the source of power is connected to the one or more ultraviolet emitters any of the electric current sensors measures zero electric current, indicating that a respective one of the one or more ultraviolet emitters has failed.

9. A method of killing pathogens on a surface, the method comprising:
    setting an intensity level;
    detecting proximity to a zone of the surface that is a target, the detecting is by one or more surface proximity detectors, wherein the detecting proximity to the zone of the surface comprises using an ultrasonic distance measurement device that detects the proximity to the zone of the surface;
    responsive to detecting proximity to the surface, controlling a flow of an electrical current proportional to the intensity level to one or more ultraviolet emitters, thereby emitting ultraviolet light at the intensity level and illuminating the surface with the ultraviolet light, the ultraviolet light producing ozone at the zone of the surface;
    delaying for a period of time; and
    disabling the one or more ultraviolet emitters, thereby stopping the emitting of the ultraviolet light and stopping production of the ozone at the zone of the surface.

10. The method of claim 9 wherein the step of controlling includes modulating the electrical current to each of the one or more ultraviolet emitters.

11. The method of claim 9 wherein the step of controlling includes providing a limited amount of the electrical current to each of the one or more ultraviolet emitters.

12. The method of claim 9, wherein the detecting proximity to the zone of the surface comprises a magnetic sensor for detecting surfaces of magnetic materials.

13. A hand-held system for killing pathogens on a surface, the hand-held system comprising:
    an enclosure;
    an intensity control, the intensity control mechanically interfaced to the enclosure;
    one or more ultraviolet emitters housed in the enclosure and covered by a filter, the filter passing ultraviolet light from the one or more ultraviolet emitters, the one or more ultraviolet emitters configured to emit ultraviolet light from the enclosure, through the filters and onto a zone of a surface, whereby ozone is produced by the ultraviolet light;
    a timer, the timer set to a predetermined period of time;
    an electrical switch configured to selectively connect a source of power to the one or more ultraviolet emitters; the electrical switch controls an electrical current provided to the one or more ultraviolet emitters proportional to a setting of the intensity control;
    means for detecting proximity to the surface that comprises one or more sensors for detecting proximity to the surface that use an ultrasonic distance measuring system; and
    responsive to the means for detecting the surface indicating contact with the surface, the timer is initiated to directly control the electrical switch and the electrical current is provided to the one or more ultraviolet emitters, the electrical current being proportional to a setting of the intensity control.

14. The hand-held system of claim 13, further comprises one or more visible light emitters housed in the enclosure and covered by the filter.

15. The hand-held system of claim 13, wherein the means for detecting proximity comprises one or more position sensors coupled to switches, the position sensors positioned at a periphery of the zone of the surface.

16. The hand-held system of claim 13, wherein the means for detecting proximity comprises a magnetic sensor.

* * * * *